US008377559B2

(12) United States Patent
Gilman

(10) Patent No.: US 8,377,559 B2
(45) Date of Patent: Feb. 19, 2013

(54) METHODS OF APPLYING A HYDROPHILIC COATING TO A SUBSTRATE, AND SUBSTRATES HAVING A HYDROPHILIC COATING

(75) Inventor: Thomas H. Gilman, Spring Grove, IL (US)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 13/243,942

(22) Filed: Sep. 23, 2011

(65) Prior Publication Data

US 2012/0015192 A1 Jan. 19, 2012

Related U.S. Application Data

(62) Division of application No. 11/699,663, filed on Jan. 30, 2007, now Pat. No. 8,053,030.

(60) Provisional application No. 60/764,151, filed on Feb. 1, 2006.

(51) Int. Cl.
*B32B 9/04* (2006.01)
*B32B 17/10* (2006.01)
*B32B 17/40* (2006.01)

(52) U.S. Cl. ............... 428/411.1; 428/409; 428/420; 428/424.4

(58) Field of Classification Search ............ 428/409, 428/420, 424.2, 424.4, 411.1
See application file for complete search history.

(56) References Cited

U.S. PATENT DOCUMENTS

| | | | |
|---|---|---|---|
| 4,302,553 A | 11/1981 | Frisch et al. ............ 525/28 |
| 4,423,099 A | 12/1983 | Mueller et al. ............ 428/35.2 |
| 4,589,873 A | 5/1986 | Schwartz et al. ............ 604/265 |
| 4,642,267 A | 2/1987 | Creasy et al. ............ 428/413 |
| 4,840,851 A | 6/1989 | Golander et al. ............ 428/523 |
| 4,872,867 A | 10/1989 | Joh et al. ............ 604/269 |
| 4,876,126 A | 10/1989 | Takemura et al. ............ 428/35.7 |
| 4,990,357 A | 2/1991 | Karakelle et al. ............ 427/2.12 |
| 5,090,406 A * | 2/1992 | Gilman ............ 602/47 |
| 5,295,978 A | 3/1994 | Fan et al. ............ 604/265 |
| 5,331,027 A | 7/1994 | Whitbourne ............ 524/37 |
| 5,576,072 A | 11/1996 | Hostettler et al. ............ 427/532 |
| 5,603,991 A | 2/1997 | Kupiecki et al. ............ 427/508 |
| 5,670,558 A | 9/1997 | Onishi et al. ............ 523/112 |
| 5,702,754 A | 12/1997 | Zhong ............ 427/2.12 |
| 5,776,611 A | 7/1998 | Elton et al. ............ 428/423.1 |
| 5,804,318 A | 9/1998 | Pinchuk et al. ............ 428/421 |
| 5,871,823 A | 2/1999 | Anders et al. ............ 427/512 |
| 5,932,299 A | 8/1999 | Katoot ............ 427/508 |
| 6,007,876 A | 12/1999 | Niino ............ 427/508 |
| 6,017,577 A | 1/2000 | Hostettler et al. ............ 427/2.12 |
| 6,048,620 A | 4/2000 | Zhong et al. ............ 428/424.4 |
| 6,110,483 A | 8/2000 | Whitbourne et al. ........ 424/423 |
| 6,156,344 A | 12/2000 | Kim et al. ............ 424/484 |
| 6,187,369 B1 | 2/2001 | Beavers ............ 427/2.24 |
| 6,211,249 B1 | 4/2001 | Cohn et al. ............ 514/772.1 |
| 6,221,425 B1 | 4/2001 | Michal et al. ............ 427/2.25 |
| 6,238,799 B1 | 5/2001 | Opolski ............ 428/423.1 |
| 6,261,630 B1 | 7/2001 | Nazarova et al. ............ 427/2.12 |
| 6,540,698 B1 | 4/2003 | Ishii et al. ............ 600/585 |
| 6,673,385 B1 | 1/2004 | Ding et al. ............ 427/2.28 |
| 6,673,453 B2 | 1/2004 | Beavers et al. ............ 428/420 |
| 6,780,504 B2 | 8/2004 | Rupprecht et al. ............ 428/354 |
| 6,828,028 B1 * | 12/2004 | Fukui et al. ............ 428/413 |
| 6,835,410 B2 | 12/2004 | Chabrecek et al. ............ 427/2.24 |
| 7,008,979 B2 * | 3/2006 | Schottman et al. ............ 523/334 |
| 2003/0100666 A1 | 5/2003 | DeGroot et al. ............ 524/555 |
| 2004/0001892 A1 | 1/2004 | Healy et al. ............ 424/486 |
| 2004/0086722 A1 | 5/2004 | Madsen ............ 428/423.3 |
| 2005/0228115 A1 | 10/2005 | Auguste et al. ............ 524/505 |
| 2007/0016169 A1 | 1/2007 | Utas et al. ............ 604/544 |
| 2007/0149929 A1 | 6/2007 | Utas et al. ............ 604/172 |

FOREIGN PATENT DOCUMENTS

| | | |
|---|---|---|
| CA | 2426251 | 4/2002 |
| CN | 1106744 | 8/1995 |
| EP | 0 379 156 | 4/1996 |
| EP | 1 103 278 | 5/2001 |
| EP | 1 745 807 | 1/2007 |
| JP | 0833704 | 2/1996 |
| WO | 92/13718 | 8/1992 |
| WO | 98/58988 | 12/1998 |
| WO | 98/58990 | 12/1998 |
| WO | 99/02141 | 1/1999 |
| WO | 99/11728 | 3/1999 |
| WO | 99/14282 | 3/1999 |
| WO | 99/57201 | 11/1999 |
| WO | 03/087254 | 10/2003 |
| WO | 2006/117372 | 11/2006 |
| WO | 2007/011287 | 1/2007 |

OTHER PUBLICATIONS

European Patent Application Publication No. EP 2 289 573 A3 dated May 18, 2011 (publication of European Search Report for European Application No. 10195654.8).
Search Report and Written Opinion for European Application No. 10195654.8, dated Apr. 19, 2011.
DuPont Packaging & Industrial Polymers, "DuPont™ Elvax® CM3326," 1995-2004.
DuPont Packaging & Industrial Polymers, "DuPont™ Nucrel® 2806," 1995-2004.
DuPont®, "Injection Moulding Guide," Hytrel® Engineering Thermoplastic Elastomer, pp. 1-24 (1997).
DuPont®, "Rheology and Handling," Product Information, pp. 1-8 (1993).
DuPont™ Nucrel®, "DuPont™ Nucrel® ," Retrieved from the Internet on Jan. 17, 2007: <URL:http://www/2.dupont.com/Products/en_RU/Nucrel_en.html>.
Estane® Thermoplastic Polyurethane TPU, "Product Information," Retrieved from the Internet on Jan. 17, 2007: <URL:http://www.estane.com/featuresBenefits/overview.asp>.
Noveon The Specially Chemicals Innovator™, "Noveon's Family of TPUs,".
Noveon The Specialty Chemicals Innovator™, "Thermedics™ Polymer Products," Retrieved from the Internet on Jan. 17, 2007: <URL:http://www.estane.com/relatedProducts/ThermedicsOverview.asp>.

(Continued)

*Primary Examiner* — Thao T. Tran
(74) *Attorney, Agent, or Firm* — Cook Alex Ltd.

(57) ABSTRACT

This invention relates to methods of applying to a substrate a hydrophilic coating that becomes lubricious when activated with water or water vapor, and to substrates having such a hydrophilic coating.

8 Claims, No Drawings

OTHER PUBLICATIONS

Noveon, The Specialty chemical Innovator™, "Overview," Product Information, Estane® Thermoplastic Polyurethane TPU, Retreived from the Internet on Jan. 17, 2007: <URL:http://www.estane.com/featuresBenefits/overview.asp>.

Pebax Basis of Performance, "What are Pebax® Breathable Films?" Breathable Films, pp. 1-7 (2002).

Sartomer, "Applicable Product Line(s)," Retrieved from the Internet on Jan. 17, 2007: <URL:http://www.sartomer.com/prodselectview.asp?sa=1&apid=2&plid=3&sgid=27>.

Sartomer, "Oligo (2-Hydroxy-2-Methyl-1-4 (1-Methylvinyl) Propanone and 2-Hydroxy-2-Methyl-1-Phenyl Propan-1-One (Monomeric)," Product Bulletin: Esacure KIP 150, p. 1.

Sartomer, "Product Detail: Esacure KIP 150," Retrieved from the Internet on Jan. 16, 2008: <URL:http://www.sartomer.com/proddetail.asp?plid=3&sgid=27&prid=ESACURE+KIP+150>.

Ward, "Medical Plastics Thermoplastic Silicone-Urethane Copolymers: A New Class of Biomedical Elastomers," Medical Device Link (2000). Retrieved from the Internet on Jan. 11, 2008: <URL:http://www.devicelink.com/mddi/archive/00/04/011.html>.

International Preliminary Report on Patentability for International Application No. PCT/US2007/002545, dated Aug. 5, 2008.

International Search Report for International Application No. PCT/US2007/002545, dated Jun. 9, 2008.

Written Opinion for International Application No. PCT/US2007/002545, dated Jun. 9, 2008.

European Office Action for European Application No. 07 762 800.6, dated Oct. 13, 2009.

European Office Action for European Patent Application No. 07 762 800.6, dated Dec. 23, 2008.

European Search Report for European Application No. 1019565.48, dated May 23, 2011.

Decision to refuse European patent application for corresponding European Patent Application No. 07762800.6, dated Jul. 13, 2011.

* cited by examiner

US 8,377,559 B2

METHODS OF APPLYING A HYDROPHILIC COATING TO A SUBSTRATE, AND SUBSTRATES HAVING A HYDROPHILIC COATING

CROSS-REFERENCE TO RELATED APPLICATION

This is a division of U.S. patent application Ser. No. 11/699,663, filed Jan. 30, 2007, which claims the priority benefit under 35 U.S.C. §119(e) of U.S. provisional patent application Ser. No. 60/764,151, filed Feb. 1, 2006, the entire disclosure of which is incorporated herein by reference, is hereby claimed.

FIELD OF THE INVENTION

This invention relates to methods of applying to a substrate a hydrophilic coating that becomes lubricious when activated with water or water vapor, and to substrates having such a hydrophilic coating.

BACKGROUND

In the medical field, and in other fields as well, there has developed a need for substrates with surfaces that become lubricious upon contact with water. A main use of lubricious materials involves catheters, catheter guide wires, and other medical devices that are meant to be inserted into the body. The lubricious nature of such materials allows the insertion (and subsequent removal) of a catheter or other medical device to be accomplished with minimum resistance, thereby reducing discomfort and possible injury.

In many cases, it is easy to prepare a functional lubricious coating for a substrate surface. However, it is more difficult to prepare a lubricious coating that is securely anchored to the substrate surface. Secure anchoring of a lubricious coating to a substrate surface is generally desirable, and particularly useful in the medical field, where secure anchorage of the coating is often an important requirement.

U.S. Pat. No. 4,642,267 to Creasy et al. discloses a hydrophilic polymer blend comprising a thermoplastic polyurethane and a poly(N-vinyl lactam). When used as a coating material, the polymer blend components are co-dissolved in an organic solvent capable of solubilizing both polymers, a substrate is dip coated in the solution, and the solvent is then driven off by a drying process so as to form a hydrophilic coating on the substrate surface. However, the coating attachment to the substrate is considered to lack the security desired. Another disadvantage of the '267 patent is that high boiling point and potentially toxic solvents are used to deliver the coating formulation, and thus significant costs must be incurred to drive off the solvent residuals from the coated product so as to obtain the desired biocompatibility.

U.S. Pat. No. 5,702,754 to Zhong discloses coating a substrate surface with a polymer having reactive functional groups and an excess of cross-linking agent. The polymer is cured to form a coating. Then, a second coating comprising a hydrophilic polymer having the same type of reactive functional groups is applied thereover. When the hydrophilic polymer is then cured, the second coating becomes covalently bonded to the first coating because the first coating includes an excess of cross-linking agent thereby permitting covalent bonding between the first coating and the hydrophilic polymer. Disadvantages of this approach include the fact that multiple steps are required and multiple polymer solutions are involved. There are also significant limitations in the selection of lubricious polymers and cross-linking agents.

SUMMARY OF THE INVENTION

In one aspect, the invention provides a method of applying a hydrophilic coating to a substrate having a surface comprised at least in part of a water-swellable material, and contacting the substrate surface with a solution comprising at least one of (i) a water-soluble polymer capable of being cross-linked to form a cross-linked, lubricious, hydrophilic coating and (ii) a water-soluble monomer capable of being polymerized to form a cross-linked, lubricious, hydrophilic coating. The water-soluble polymer can be cross-linked in the presence of the swollen substrate surface to provide a cross-linked coating that is entangled with and securely anchored to the substrate surface. Similarly, the monomer can either form a crosslinked hydrogel network as it is polymerized, or can be polymerized and then subsequently cross-linked, in the presence of the swollen substrate surface, to provide a cross-linked coating that is entangled with and securely anchored to the substrate surface. The substrate includes a first or outer layer comprising a water-swellable material. The substrate may further include an optional second or support layer, which comprises non-water-swellable materials and/or water-swellable materials.

In another aspect, the invention provides a substrate having a hydrophilic coating, such substrate, prior to coating, having a surface comprised at least in part of a water-swellable material having swollen and non-swollen states, and the coating comprises an interpenetrating polymer network disposed on at least a part of the surface, the interpenetrating polymer network formed by at least one of (i) a water-soluble polymer capable of being cross-linked to form a cross-linked, lubricious, hydrophilic coating and (ii) a water-soluble monomer capable of being polymerized to form a cross-linked, lubricious, hydrophilic coating, in the presence of the swollen state of the surface, so as to secure the hydrophilic coating to the surface.

DETAILED DESCRIPTION

One aspect of the invention relates to methods of applying a lubricious, hydrophilic coating to a substrate. An additional aspect of the invention relates to substrates having such a lubricious, hydrophilic coating.

As used herein, the term "lubricious coating" refers to a coating that provides a substrate surface having a coefficient of friction value less than about 0.3, less than about 0.1, and/or less than about 0.05, for example, 0.03, or even 0.01.

The invention involves creating an interpenetrating polymer network in situ on a substrate surface. For example, a substrate surface comprising a water-swellable material is contacted with a solution comprising a water-soluble hydrophilic polymer capable of being cross-linked to form a cross-linked, lubricious hydrophilic coating. Alternatively, a water-soluble monomer, either capable of being polymerized to form a cross-linked, lubricious, hydrophilic coating, or of being polymerized and then cross-linked to form a cross-linked, lubricious, hydrophilic coating, may be used in place of, or in addition to, the water-soluble hydrophilic polymer. The coating is typically then cured, for example, by exposure to UV light, in order to cross-link the water-soluble polymer and/or polymer formed from the water-soluble monomer.

The use of one or more water-soluble polymers is typically preferred relative to the use of one or more water-soluble monomers, however, particularly for medical applications, because residual unpolymerized monomer can present biocompatibility issues for medical device applications.

Because the water-swellable material of the substrate swells in the presence of water and/or alcohol, it is believed to become physically entangled with the water-soluble hydrophilic polymer before cross-linking, and those entanglements are locked in during cross-linking. Thus, a coating comprising the interpenetrating polymer network is formed by polymerizing the water-soluble polymer in the presence of the water-swellable substrate surface when the water-swellable substrate surface is in a swollen state, and results in the lubricious coating being securely anchored to the substrate (after cross-linking thereof). Essentially, the method allows two hydrogels to be linked together mechanically on a molecular scale.

Advantageously, the hydrophilic coating can be secured to the surface without the need for covalent interactions between the hydrophilic coating and the first layer. Another advantage is that the coating formulation can be carried using solvents such as water and lower alcohols, which are inexpensive, biocompatible, and relatively easy to drive off from the coated product. Still another advantage is the versatility of the invention; the invention will provide secure anchorage for any hydrophilic coating formed from a water-soluble polymer and/or water-soluble monomer, which can be coated from an aqueous or alcohol based solution, without the need for a primer layer or other polymer solution based anchorage means. This versatility allows a wide number of polymer/cross-linking agent systems and/or monomer/initiator/cross-linking systems to be utilized, and thus for an optimal system to be implemented for any given application.

In one embodiment, the terms "well-anchored" or "securely anchored" refers to a coating that, after an abrasion protocol is conducted on the substrate carrying the coating, results in a substrate having a final coefficient of friction value, when the coating is activated, for example, by water immersion, that is not more than ten times, not more than five times, and/or not more than two times the original coefficient of friction value prior to abrasion. A suitable abrasion protocol includes passing a coated tube through a hole which is about 10% smaller diameter than the outside diameter of the tubing 100 times, while keeping the coating wet during the abrasion cycles. After this abrasion protocol, the tube is immersed in deionized water for about 30 seconds so as to activate the coating, and the coefficient of friction can be determined using standard means.

A substrate, such as a catheter tube, to be coated by the methods of this invention, is formed in a way that provides it with a surface or surface layer comprised at least in part of a water-swellable material. That may be accomplished in a variety of ways including but not limited to coextruding a substrate having a first or outer layer comprising any suitable water-swellable material, and a second or inner support layer comprised of non-water-swellable materials and/or water-swellable materials.

Generally, any water swellable-materials or mixtures thereof could be used for the first or outer layer. Suitable water-swellable materials include but are not limited to water-swellable polyamide-based copolymers, water-swellable polyester-based copolymers, water-swellable urethane-based copolymers, and mixtures thereof. Any of a variety of thermoplastic polymers, thermoplastic elastomers, and/or thermoplastic alloys, which are capable of swelling in the presence of water (e.g., an aqueous solution) may be used. In general, such water swellable polymers will also swell in lower alcohols such as methanol, ethanol, propanol, isopropanol, butanol, and the like. Higher alcohols such as hexanol and octanol may also be used, but lower alcohols are typically preferred because of their increased volatility relative to water.

Preferably, the first layer is comprised of a water-swellable thermoplastic elastomer comprising a block copolymer having rigid and flexible blocks. Suitable rigid blocks include polyamide blocks, polyester blocks, and polyurethane blocks, but other rigid polymer blocks may be used. The rigid block is preferably either glassy or crystalline at room temperature. Suitable flexible blocks include flexible polyether blocks such as flexible polyethylene oxide blocks, flexible poly-N-vinyl lactam blocks such as flexible polyvinylpyrrolidone blocks, flexible polyalcohol blocks, and flexible polyacid blocks. Of course, other flexible blocks could also be used.

Suitable water-swellable thermoplastic elastomers include but are not limited to polyether/polyamide block elastomers such as those sold under the PEBAX® trade name (Arkema, PA), for example, such as PEBAX® 1647, PEBAX® 1074, and PEBAX® MX1652, and polyester elastomers such as those sold under the HYTREL® trade name (Du Pont de Nemours, DE), for example, such as HYTREL® 8171 and HYTREL® 8206. Other suitable water-swellable thermoplastic elastomers include but are not limited to thermoplastic polyurethanes such as polyether thermoplastic polyurethanes sold under the ESTANE® and the TECOPHILIC® trade names (Noveon Inc., OH) and polyester thermoplastic polyurethanes such as those sold under the ESTANE® and CARBOTHANE® trade names (Noveon Inc., OH).

The substrate can be made entirely from a water-swellable material. Polymer blends including at least one water-swellable material can alternatively be used. Surprisingly, even polymer blends where a water-swellable material comprises only a minority of the polymer blend will provide securely anchored hydrophilic coatings. This allows flexibility in designing substrates, for example, as a homoextrusion that will have the mechanical properties needed for a given application. For example, tubing made of 40 weight percent (wt. %) PEBAX® 1074 (a water-swellable thermoplastic elastomer) and 60 wt. % PEBAX® 3533 (a non-water-swellable thermoplastic elastomer) has desirable properties for a urinary catheter application, and provides many or all of the advantages of this invention.

Alternatively, the substrate can have an outer layer made from a water-swellable material, or an outer layer made from a blend comprised of water-swellable and non-water-swellable materials. The substrate can then have an inner or support layer comprised of one or more non-water-swellable materials. Of course, the inner or support layer may be made from or further include one or more water-swellable materials.

As used herein, the term "water-swellable" generally refers to a material that swells in the presence of water or alcohol. In various embodiments, the term refers to a material that increases in at least one dimension by at least 0.5%, at least 1%, at least 2%, at least 5%, at least 10%, at least 25%, or even greater when immersed in water for a period of approximately 90 minutes. In accordance with the foregoing embodiments, a 1 inch by 1 inch by 1 mil square of material can be immersed in water for a period of 90 minutes, and the increase in the height or length can be determined relative to the original height or length so as to ascertain whether a certain material swells sufficiently to be considered a water-swellable material in accordance with the invention. If so, the material can generally be considered suitable for use as a water-swellable material in the invention.

Generally, any material can be used in forming the optional second or support layer, but materials capable of being extruded or otherwise melt-processed are generally preferred. Suitable materials for use in the optional second or support layer include but are not limited to thermoplastic resins, such as, for example, olefin polymers, particularly, polyethylenes, polypropylenes, polyvinylchlorides, polytetrafluoroethylenes, polyvinylacetates, polystyrenes, polyesters, polyurethanes, polyamides, other suitable polymers, and mixtures thereof. Metals, ceramics, and other materials may also be used as the support layer, but then the outer layer needs to be affixed or coupled to the second layer by a mechanism different than co-extrusion, for example, by spin-casting, dip-coating, wire extrusion coating, or otherwise affixing, coupling, or adhering the water-swellable surface layer (or substrate comprising same) to the second layer.

The substrate can be a medical device. Exemplary medical devices that may be coated with the lubricious coatings in accordance with the invention include but are not limited to contact lenses, medical implants including but not limited to pacemakers and wire leads for same, intravascular implants including but not limited to arterial stents, and catheters including but not limited to urinary catheters, fecal catheters, catheters for administration of intravenous fluids, medications, and nutrition, and coronary catheters such as angioplasty catheters. Further still, in certain medical device applications it may be desirable to incorporate a drug into the coating solution, or to add a drug after formation of the coating on the medical device. For example, stents having a coating in accordance with the invention can comprise a drug, for example, taxol to prevent late stenosis, or heparin to prevent the formation of a thrombus.

Additionally, non-medical device applications of the invention can also be envisioned where surfaces having a low coefficient of friction in a wet environment are desired because the invention can provide a highly lubricious coating to any product that is used in a wet environment. Possible non-limiting examples include marine uses, for example, such as wet suits or boat hulls where the coating could be applied to reduce drag.

The untreated substrate is typically dipped or otherwise coated with a polymer solution in which the coating polymer is dissolved in water, alcohol, or a solution containing both water and alcohol. If a catheter is being coated, a mandrel can be inserted into the catheter structure in order to prevent any coating solution from contacting and/or coating the inside of the catheter when the coating solution is applied.

Any suitable hydrophilic polymer capable of being cross-linked and of swelling and becoming lubricious when exposed to water or water vapor may be used to provide the hydrophilic coating. Upon being cross-linked, the network of the coating polymer forms an interpolymer with the swollen water-swellable material, for example, with the flexible (or soft) blocks of the substrate surface block polymer, resulting in a coating that is securely anchored to the substrate. Suitable water-soluble hydrophilic polymers include but are not limited to polyacrylic acids, acrylic acid copolymers such as acrylamide/acrylic acid copolymers, polyvinylpyrrolidones, polyvinylalcohols, water-soluble polymers containing carboxylic acid functional groups, and mixtures thereof. Other water-soluble polymers that can be cross-linked to form a hydrophilic coating may also be used.

Similarly, any suitable hydrophilic monomer capable of being polymerized to form a cross-linked network and becoming lubricious when exposed to water or water vapor may be used to provide the hydrophilic coating. Suitable water-soluble hydrophilic monomers that can be used include but are not limited to vinyl monomers, for example, vinyl alcohols, vinylpyrollidones, acrylamides, methacrylates, acrylic acids, and mixtures thereof. Some of these can be copolymerized with multifunctional monomer to form a network in situ, others can be polymerized and subsequently cross-linked using methods well known in the art. Various initiators, for example, photoinitiators including but not limited to benzophenone can be used to polymerize the monomers.

An important advantage of this method is that it is relatively easy to prepare a substrate with a securely anchored hydrophilic coating. Since the outer layer of the substrate generally includes a thermoplastic polymer, known manufacturing methods that are uncomplicated, direct, and economical, such as extrusion, co-extrusion, or injection molding, may be used to produce a substrate having a water-swellable surface. The coating method is applicable to any system of hydrophilic coating polymer and cross-linking method that can be achieved using a water- or alcohol-based solvent system. Similarly, the coating method is applicable to any system of hydrophilic monomer, initiator, and cross-linking method that can be achieved using a water- or alcohol-based solvent system.

Suitable cross-linking agents are well known in the art and include but are not limited to UV activatable cross-linking agents, carbodiimides, aziridines, melamine formaldehydes, and multifunctional carboxylic acid cross-linking agents. Exemplary UV activatable cross-linking agents include polymeric hydroxyl ketones sold under the ESACURE™ trade name (Sartomer Company, PA), for example, ESACURE™ KIP 150 and ESACURE™ ONE. Exemplary carbodiimide cross-linking agents are sold under the CARBODILITE™ trade name (Nisshinbo Industries, Inc., JP), for example, CARBODILITE™ V-02-L2 and CARBODILITE™ E-02. Exemplary aziridine cross-linking agents are sold under the cross-linker CX-100 trade name (DSM NeoResins, DSM, NL). Heat and/or light can also be used to cross-link some water-soluble polymers.

The methods of applying a hydrophilic coating to a substrate and substrates having such a hydrophilic coating in accordance with the invention can be better understood in light of the following examples. However, the foregoing description and the following examples are merely illustrative, and therefore no unnecessary limitations should be understood therefrom as numerous modifications and variations are expected to occur to those skilled in the art.

EXAMPLE 1

A coating polymer solution was prepared in an approximately 70:30 weight/weight isopropyl alcohol/water solvent system, where the polymer was polyvinylpyrrolidone K-90 at about 9 wt./vol. Included in the solution was about 0.03 wt. % UV activatable cross-linking agent (ESACURE™ KIP 150, Sartomer).

A thermoplastic substrate was employed in the form of a coextruded tube having an outside diameter of about 0.180 inches and an inside diameter of about 0.123 inches. The tube had an outer layer of about 0.003 inches thick that was a blend of a polyether/polyamide block elastomer (PEBAX® 1074, a water-swellable thermoplastic elastomer available from Arkema, PA) with an ethylene acid copolymer resin (NU-CREL® 2806, a non-water-swellable thermoplastic elastomer available from Du Pont de Nemours, DE) at a weight ratio of about 40:60. The inner layer of the tube was a blend of thermoplastic, non-water-swellable resins designed to give the desired mechanical properties to the overall tube structure. The tube was dipped in the coating solution and held therein for about 10 minutes prior to withdrawal. After withdrawal, the tube was air dried for about 30 minutes. Thereafter, the coated tube was exposed to UV light for about 5 minutes.

The tube with its cured coating was immersed in deionized water for 30 seconds. At that point, the surface of the tube was found to be highly lubricious, and the lubricious coating was securely adhered to the tube.

EXAMPLE 2

Another approach is to use a separate, second solution that contains a cross-linking agent for the coating polymer. The second solution can be applied to the substrate having a water-swellable outer surface either before, or after, the coating polymer solution is applied. After both solutions have been applied, the coating is then cross-linked.

A coextruded tube was prepared having an outer layer of a polyether/polyamide block elastomer (PEBAX® 1074, Arkema, PA), and an inner layer of a polyether/polyamide block elastomer (PEBAX® 2533, a non-water-swellable thermoplastic elastomer available from Arkema, PA). The tube was first dipped in an approximately 70:30 weight/weight isopropyl alcohol/water solution containing about 12 wt. % of a carbodiimide cross-linking agent (CARBODILITE™ V-02-L2, Nisshinbo, Japan), and held therein for ten minutes prior to withdrawal. The tube was then air dried for ten minutes, subsequently dipped in an approximately 70:30 weight/weight isopropyl alcohol/water solution containing about 7.5 wt. % of a water-soluble polymer containing carboxylic acid functional groups (GANTREZ™ S-97BF, ISP Technologies, Inc.), and then withdrawn immediately. After withdrawal, the tube was air dried for ten minutes.

The water-soluble polymer of this example is a methyl vinyl ether copolymer with maleic anhydride where the anhydride has been hydrolyzed into a diacid. The acid groups can be cross-linked by the carbodiimide cross-linking agent.

Curing was accomplished by heating the tubing to approximately 70° C. for about 20 minutes in a conventional oven. The coating was neutralized by dipping it in a buffer solution. The resulting tube with its cured coating was then dipped in deionized water for 30 seconds. The surface of the wetted tube was slippery and the coating was securely adhered to the tube.

EXAMPLE 3

A thermoplastic substrate was employed in the form of a coextruded tube having an outside diameter of about 0.181 inches and an inside diameter of about 0.122 inches. The tube had an outer layer of about 0.003 inches thick, with the inner layer accounting for the balance of the tube. The inner tube layer comprised a blend of an ethylene octene copolymer (EXACT™ 5371, ExxonMobil Chemical Company, ExxonMobil, TX) with an ethylene acid copolymer resin (NUCREL® 2806, Du Pont de Nemours, DE) at a weight ratio of approximately 20:80, and the outer tube layer comprised a blend of a polyether/polyamide block elastomer (PEBAX® 1074, Arkema, PA) with an ethylene acid copolymer resin (NUCREL® 2806, Du Pont de Nemours, DE) at a weight ratio of approximately 40:60.

The tubing was coated by dipping in an approximately 70:30 weight/weight isopropyl alcohol/water solution containing about 5.5 wt. % polyvinylpyrollidone K-90 (ICI Chemicals, England) and about 0.11 wt. % ESACURE™ One (Sartomer, PA). The tubing was held in the coating solution for about 5 minutes in this solution and then withdrawn. After withdrawal, the coated tubing was air dried for about 50 minutes (at room temperature). Thereafter, the coated tube was exposed to UVC light for approximately 2.5 minutes.

The resulting tube with its cured coating was then immersed in deionized water for about 30 seconds. At that point, the surface of the tube was found to be highly lubricious, having an average coefficient of friction (n=12 samples tested) of about 0.02.

To test coating anchorage to the substrate tubing, an abrasion testing protocol was performed on the resulting coated tubing. The sample was passed through a hole in a 1/32" thick silicone rubber sheet, with the hole being about 10% smaller diameter than the outside diameter of the tubing. This was done 100 times, keeping the coating wet during the abrasion testing. After this abrasion protocol, the tube was again immersed in deionized water for about 30 seconds and tested for coefficient of friction. Again, the average coefficient of friction for the samples was about 0.02.

Another group of samples was immersed for about 30 seconds in water to activate the coating, and then allowed to stand out in open air for about 10 minutes. Following this drying protocol, the average coefficient of friction (n=12 samples tested) was about 0.02.

Still another group of samples (n=three samples) were subjected to a thermoforming process to create a bullet shaped closed tip on one end in order to make a tipped tube suitable for use as a urinary catheter. This tipped tubing was subjected to a coating process as described in this example above, except the cure was by accomplished by exposure to UVC light for a period of about 3 minutes. After immersion in deionized water for about 20 minutes, the surface of the coated tubing was very slippery and the slippery coating was well adhered to both the formed tip portion of the tubing and the straight wall portion of the tubing.

The foregoing examples demonstrate several advantages of the invention. For example, highly lubricious, highly adherent coatings have been achieved with two different water soluble polymer/cross-linker systems, and with three different substrate constructions. Example 3 further demonstrates that it is possible to thermoform a multi-layered tube while maintaining the water-swellable properties of the outer layer surface, which allows a securely anchored coating to be achieved, even in the formed portion of the substrate. Example 3 also demonstrates that coatings made per this invention are able to maintain their slippery nature even after an extended period of air exposure. It is theorized that the water-swellable nature of the substrate surface helps in this regard, as the substrate surface will hold water and thus perhaps contribute to the ability of the coating to maintain hydration and therefore lubricity. This attribute of the invention is particularly advantageous for intermittent urinary catheters.

While embodiments of this invention have been disclosed in considerable detail herein for purposes of illustration, it will be understood by those skilled in the art that many of those details may be varied without departing from the spirit and scope of the invention. Accordingly, only such limitations as appear in the appended claims should be placed on the invention.

What is claimed is:
1. A coated substrate comprising:
   a substrate having a surface, wherein at least a portion of the surface is water-swellable; and,
   a cross-linked hydrophilic coating disposed on the surface wherein the cross-linked hydrophilic coating is physically entangled with the water-swellable portion of the substrate surface to form an interpenetrating polymer network which anchors the cross-linked hydrophilic coating to the substrate.

2. The coated substrate of claim 1, wherein the substrate comprises a first layer, and a second layer, wherein at least a portion of the first layer is water-swellable material.

3. The coated substrate of claim 2, wherein the second layer is not water-swellable.

4. The coated substrate of claim 1, wherein the coated substrate comprises a substrate of a medical device.

5. The coated substrate of claim 4, wherein the medical device is selected from the group consisting of medical implants, intravascular implants, catheters, and contact lenses.

6. The coated substrate of claim 1, wherein the cross-linked hydrophilic coating physically entangled with the water-swellable portion of the substrate to form the interpenetrating polymer network comprises at least one of (i) a cross-linked water-soluble polymer and (ii) a polymerized water-soluble monomer.

7. The coated substrate of claim 6, wherein the portion of the water-swellable substrate surface material comprises a block copolymer selected from the group consisting of water-swellable polyamide-based copolymers, water-swellable polyester-based copolymers, water-swellable urethane-based copolymers, and mixtures thereof.

8. The coated substrate of claim 6, wherein the water-soluble polymer is selected from the group consisting of polyacrylic acids, acrylic acid copolymers, poly-N-vinyl lactams, polyvinylalcohols, polyvinylalcohol copolymers, and mixtures thereof.

* * * * *